(12) United States Patent
Gunderson et al.

(10) Patent No.: US 7,539,540 B2
(45) Date of Patent: May 26, 2009

(54) TROUBLESHOOTING METHODS FOR A MEDICAL SYSTEM INCLUDING IMPLANTABLE COMPONENTS

(75) Inventors: Bruce D. Gunderson, Plymouth, MN (US); Troy E. Jackson, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 272 days.

(21) Appl. No.: 11/536,364

(22) Filed: Sep. 28, 2006

(65) Prior Publication Data

US 2008/0082012 A1    Apr. 3, 2008

(51) Int. Cl.
*A61N 1/362* (2006.01)

(52) U.S. Cl. ......................... 607/27; 600/510
(58) Field of Classification Search ............... 607/1–29; 600/508–528
See application file for complete search history.

(56) References Cited

U.S. PATENT DOCUMENTS

| | | |
|---|---|---|
| 4,140,131 A | 2/1979 | Dutcher et al. |
| 5,201,865 A | 4/1993 | Kuehn |
| 5,910,156 A | 6/1999 | Cinbis et al. |
| 6,317,633 B1 | 11/2001 | Jorgenson et al. |
| 6,445,952 B1 | 9/2002 | Manrodt et al. |
| 6,721,600 B2 | 4/2004 | Jorgenson et al. |
| 2003/0204215 A1 | 10/2003 | Gunderson et al. |
| 2005/0137636 A1 | 6/2005 | Gunderson et al. |
| 2006/0116596 A1* | 6/2006 | Zhou et al. .................. 600/516 |
| 2006/0116730 A1 | 6/2006 | Gunderson |

* cited by examiner

*Primary Examiner*—Scott M Getzow
(74) *Attorney, Agent, or Firm*—Stephen W. Bauer; Michael S. Soldner

(57) ABSTRACT

A troubleshooting method can identify potential sources of noise emanating from an implanted portion of a medical system. The method, which may be carried out by the system, for example, according to pre-programmed instructions, includes a step of collecting at least one EGM sample from a sensing pair of electrodes, and an EGM sample from each of a plurality of recording pairs of electrodes. The sensing pair may be formed by first and second electrodes of an implanted lead, and the plurality of recording pairs include pairs formed by each of the lead electrodes and an electrode of an implanted device. Following collection, the EGM samples from the recording pairs may be analyzed for the presence or absence of noise and, then, potential noise sources may be determined.

18 Claims, 6 Drawing Sheets

US 7,539,540 B2

TROUBLESHOOTING METHODS FOR A MEDICAL SYSTEM INCLUDING IMPLANTABLE COMPONENTS

TECHNICAL FIELD

The present invention relates generally to medical systems including implantable components and more particularly to a method and apparatus for identifying potential sources of noise from within implantable components of the medical systems.

BACKGROUND

Implantable components of medical systems, particularly those adapted to provide cardiac pacing and/or defibrillation, often include medical devices coupled to an elongate and flexible electrical lead that carries a plurality of conductors, each of which is typically coupled to a corresponding lead electrode. An implanted cardioverter defibrillator device (ICD) can both detect and classify abnormal heart rhythms, for example, tachycardia and fibrillation, sensed by an implanted multipolar lead, and deliver the appropriate therapy, for example, pacing and/or shock therapy, according to the classification, via the same lead. ICD's may further be programmed to store electrocardiograms (EGM's) of the cardiac signal sensed by the lead over a period of time leading up to and during detection and classification of the signal and following delivery of the therapy. These EGM's can be transferred from the implanted device to an external component (e.g. a programmer/analyzer device or a remote follow-up monitor linked to a network) of the medical system for analysis by an attending physician or clinician.

In some cases the implanted lead can be subject to oversensing, that is, picking up additional signals, either cardiac or non-cardiac, that can cause the device to detect an arrhythmia which is not really present and make an improper classification leading to inappropriate therapy. Commonly assigned and co-pending U.S. patent application publication No. 2003/0204215, entitled "Method and Apparatus for Identifying Cardiac and Non-Cardiac Oversensing Using Intracardiac Electrograms", describes methods for identifying oversensing, and a series of methods for analyzing EGM's stored by an implantable device following the initial identification of oversensing.

The stored-EGM analysis methods described by U.S. 2003/0204215 serve to categorize the type of oversensing so that appropriate corrective action may be taken; the methods described can determine whether the oversensing is cardiac or non-cardiac in nature, and if non-cardiac in nature, otherwise called 'noise', whether the source of the noise is caused by oversensing of myopotentials from muscles adjacent the heart, caused by electromagnetic interference, or caused by some kind of failure that has taken place within the implantable components of the system. However, once the noise is identified as emanating from the system, there may still be questions as to the best course of corrective action. Having the capability to identify particular potential sources of noise in the system can further guide the clinician in a course of action (e.g. adding a new lead to the system to supplement or replace an implanted lead). Thus, there is a need for methods to identify potential sources of noise emanating from within implantable components of a medical system.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Constructions, materials, dimensions, and manufacturing processes suitable for making embodiments of the present are known to those of skill in the field of the invention.

Figure 1:
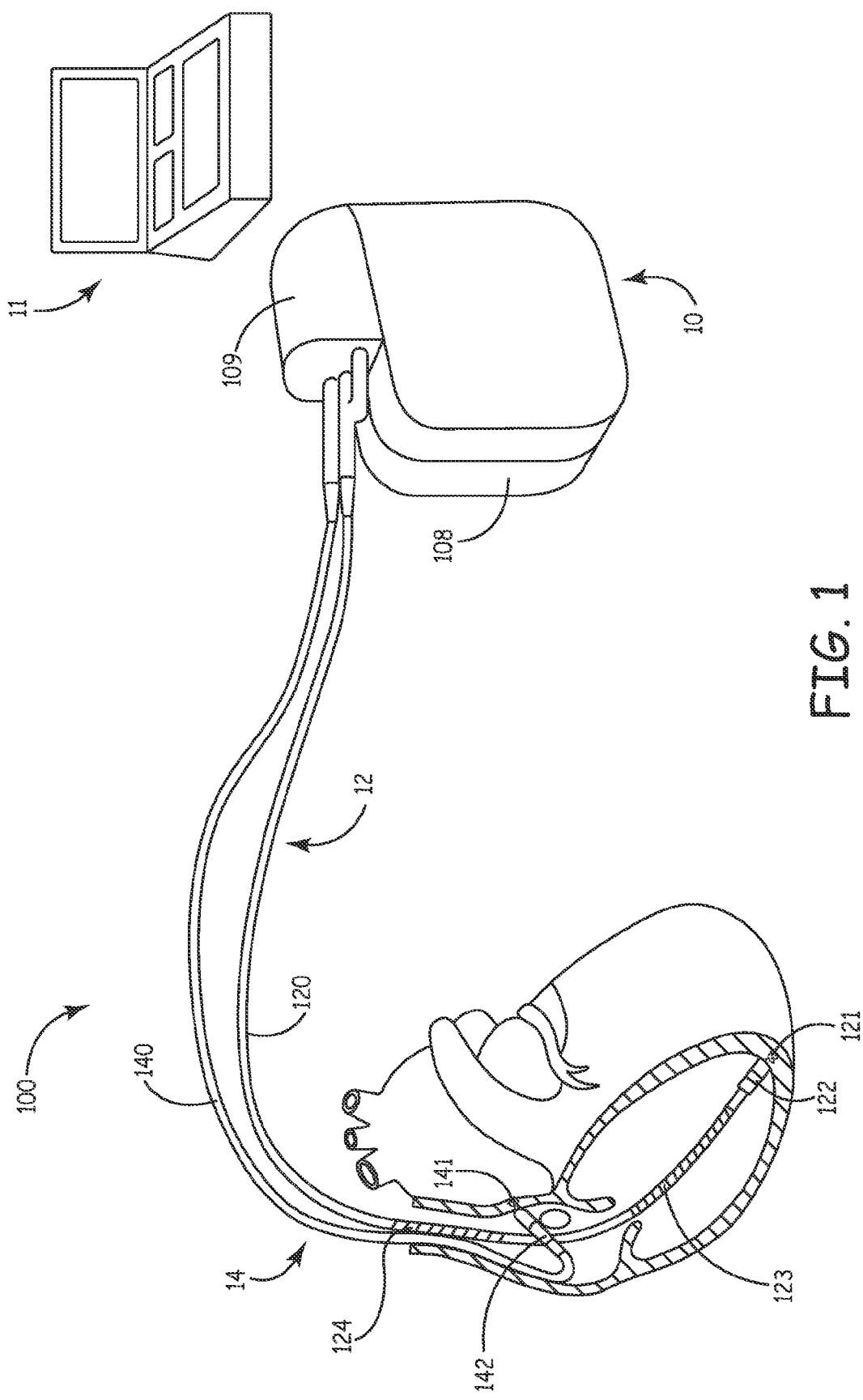
FIG. 1 is a schematic of an exemplary medical system which may incorporate embodiments of the present invention.

FIG. 1 is a schematic of an exemplary medical system 100 which is suitable for providing cardioversion and defibrillation therapy, and which may incorporate embodiments of the present invention. FIG. 1 illustrates system 100 including an implantable medical device (IMD) 10 coupled to a first medical electrical lead 12, extending into a right ventricle of a heart, and to a second medical electrical lead 14, extending into a right atrium of the heart, and an external device 11, which may be a programmer/analyzer, which has the capability to download and upload data and instructions to and from IMD 10 via telemetry, or a monitor, which has the capability to download data from IMD 10 via telemetry and to transfer the data, for example, via telemetry or a phone line, to a secure network. FIG. 1 further illustrates lead 14 including a tip electrode 141 and a ring electrode 142, forming a near-field pair for pacing and sensing in the right atrium, and lead 12 including a tip electrode 121 and a ring electrode 122, forming a near-field pair for pacing and sensing in the right ventricle; lead 12 further includes a right ventricular (RV) defibrillation coil electrode 123 and a superior vena cava (SVC) defibrillation coil electrode 124. According to the illustrated embodiment, the electrodes of each lead 12, 14 are coupled to conductors (not shown) extending within insulative bodies 120, 140 of the leads, which conductors are terminated at respective connector contacts of lead connectors (not shown), which are coupled to corresponding device contacts within a device header 109. The device contacts are coupled via sealed wire feedthroughs to electronic circuitry enclosed with a housing or a can 108 of device 10, for example at corresponding connection terminals 317, 321, 324, 326, 318 and 320 illustrated in FIG. 2.

Figure 2:
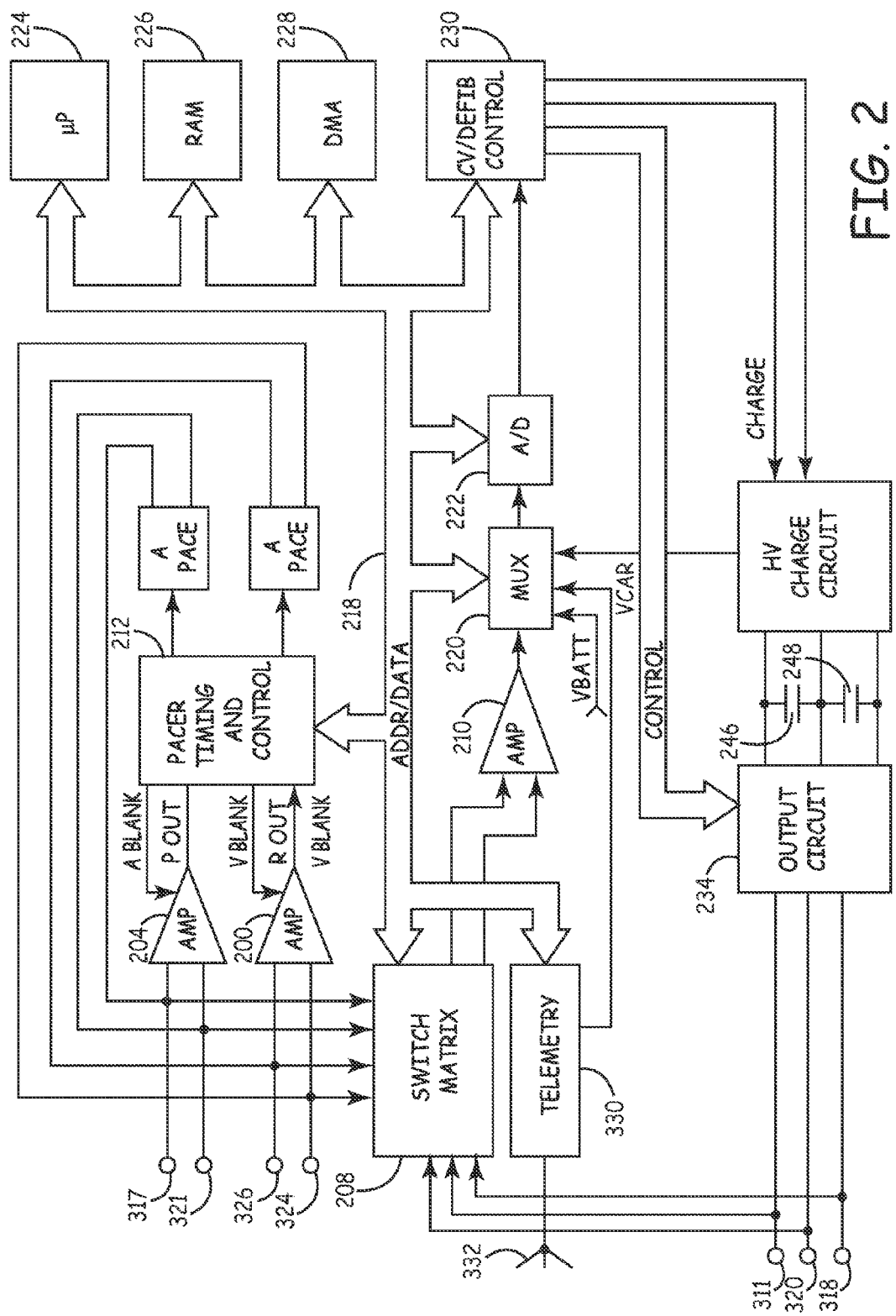
FIG. 2 is an exemplary functional block diagram for a portion of the system shown in FIG. 1.

FIG. 2 is a block diagram describing an exemplary functional arrangement of electrical components enclosed within housing 108. In addition to terminals 317, 321, 324, 326, 318 and 320 for electrical connection with each lead electrode, FIG. 2 illustrates a terminal 311 for electrical coupling with IMD housing or can 108 so that can 108 may act as an additional electrode in system 100. According to the illustrated embodiment, terminals 317 and 321 electrically connect atrial electrodes 141 and 142 to an atrial sense amplifier 204, and terminals 324 and 326 electrically connect ventricular electrodes 121 and 122 to a ventricular sense amplifier 200; each amplifier 204, 200 provides the appropriate atrial signal and ventricular signal, respectively to a pacer timing and control circuit 212 according to respective preset thresholds. FIG. 2 further illustrates each of terminals 311, 318 and 320 coupled to a high voltage output circuit 234, wherein terminal 311 provides the connection for can 108, and terminals 318 and 320 for defibrillation electrode coils 123 and 124, respectively.

With further reference to FIG. 2, a switch matrix 208, under control of a microprocessor (µP) 224, is used to select, via a data/address bus 218, the electrodes which are to be coupled to a wide band amplifier 210 for use in digital signal analysis; the signals from the selected electrodes are directed through a multiplexer 220 and thereafter converted by an A/D converter 222 for storage in random access memory (RAM) 226, which is under the control of a direct memory access (DMA) circuit 228. Microprocessor 224 includes an associated ROM for storing programs that allow microprocessor 224 to analyze signals and control the delivery of the appropriate therapy, for example, via pacing timing and control circuitry 212 and/or via cardioversion and defibrillation control circuitry 230 which initiates charging of high voltage capacitors 246, 248. Standard operation of the components shown in FIG. 2 facilitates various sensing, pacing, cardioversion and defibrillation functions, as well as methods of the present invention, and is described in greater detail in paragraphs [0036]-[0047] of aforementioned U.S. patent publication 2003/0204215, salient portions of which are hereby incorporated by reference.

Upon detection of an arrhythmia, via an EGM signal received off a sensing pair formed by the near field pair of electrodes 121 and 122 (FIG. 1), an interval of the EGM signal from the sensing pair, corresponding in time to the detection, is stored in RAM 226. Another EGM signal, from the same time period, which is sensed by a far-field pair of electrodes, for example, electrodes 121 and 123, or electrodes 123 and 124, may also be stored for comparison in order to determine if the sensing pair is oversensing. An exemplary pair of such signals is illustrated in FIG. 3.

Figure 3:
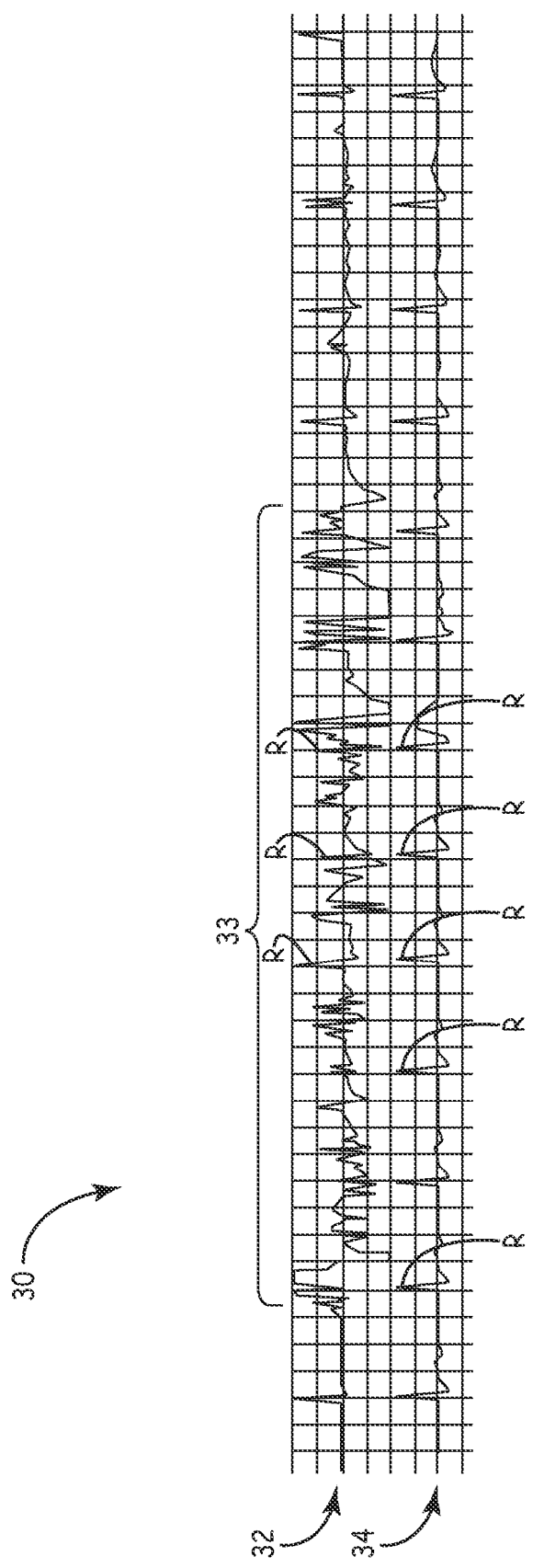
FIG. 3 is a portion of an exemplary strip chart recording including a noisy EGM signal.

FIG. 3 is a portion of a strip chart recording including an exemplary noisy EGM signal 32 collected from a sensing pair formed by a pair of near-field electrodes, for example, electrodes 121 and 122 of system 100. The illustrated recording may be generated via external device 11 (FIG. 1), which has received EGM data from IMD 10 via a telemetry circuit 330 and antenna 332 of IMD 10 (FIG. 2). FIG. 3 illustrates signal 32 alongside a concurrent far-field signal 34, so that by visual analyses, one can conclude that a portion 33 of signal 32 includes oversensing between sensed R-waves R (corresponding to ventricular depolarization). Portion 33, which may otherwise be inappropriately classified by IMD 10 as fibrillation, can be analyzed, by IMD 10 or via external device 11, according to the methods disclosed in the aforementioned '215 reference, in order to determine that portion 33 of signal 32 is caused by oversensing, that the oversensing is non-cardiac related, and thus classified as noise, and that the noise is being generated by one or more of the implanted components of system 100. Portions of the '215 reference related to such methods for identifying and classifying non-cardiac oversensing, in particular those portions associated with FIGS. 6, 7, 8, 9 and 11 thereof, are hereby incorporated by reference. Those skilled in the art, will understand that system noise, i.e. illustrated in portion 33 of signal 32, most likely emanates from lead 12, since the environment in which cardiac pacing and defibrillation leads are implanted can subject these leads to various crushing and/or bending flex forces that, over time, may cause intermittent connections within the leads, for example, due to conductor fracture and/or insulation breaches, that lead to noise. Methods, according to embodiments of the present invention, for further narrowing down the potential sources of system noise can be programmed as instructions into a system such as system 100, for example, in microprocessor 224.

Figure 4:
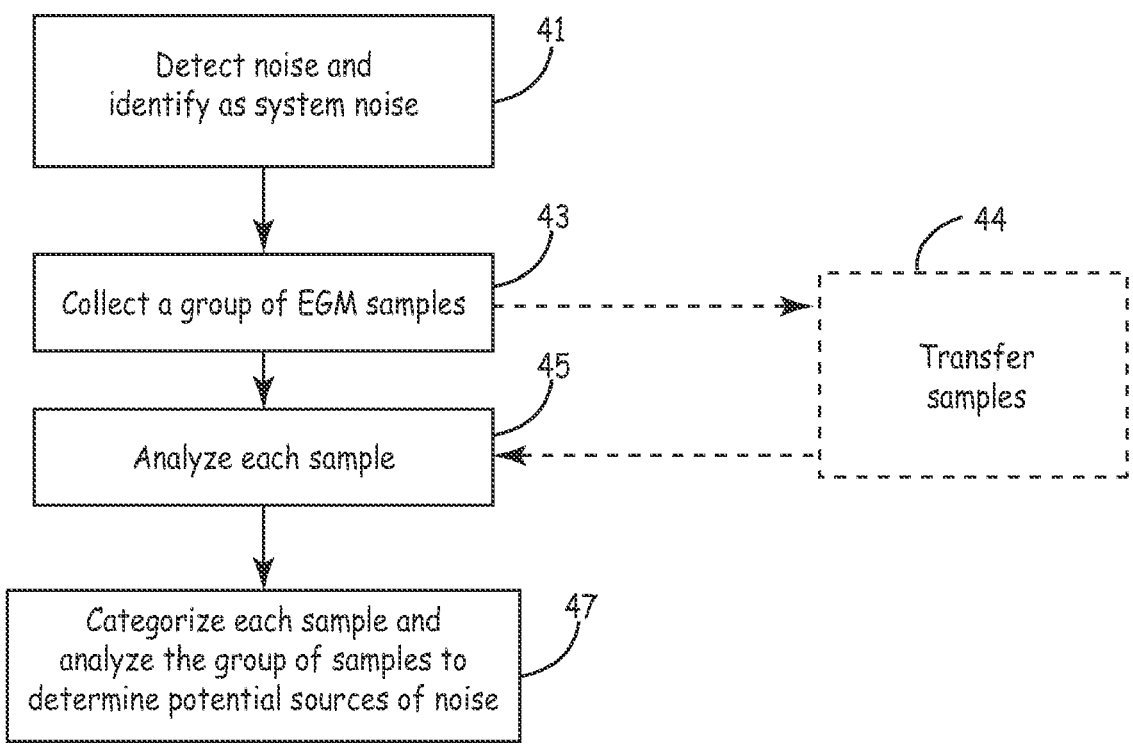
FIG. 4 is a flow chart outlining some methods of the present invention.

FIG. 4 is a flow chart outlining some methods of the present invention. FIG. 4 illustrates a preliminary step 41 in which noise is detected on a sensing pair and is then identified as system noise. Step 41 encompasses the methods of aforementioned '215 reference. The sensing pair would typically be defined as a near-field pair of electrodes essential for sensing conditions that a particular device is adapted to treat, for example, the near-field pair of electrodes 121 and 122 illustrated in FIG. 1, which are intended to be used for sensing ventricular arrhythmias. However, any other pair of electrodes may also be selected for constant monitoring, or scheduled periodic monitoring, and may thus end up as the pair on which noise is detected. An example of another pair of electrodes in system 100, that may be selected along with electrodes 121, 122 as a sensing pair, is the far-field pair of RV defibrillation coil 123 and SVC defibrillation coil 124.

Once system noise is detected, a group of EGM samples are collected, per step 43, in order to start narrowing down potential sources of the noise. According to embodiments of the present invention, the EGM samples are collected from the sensing pair on which noise was originally detected and from what will be denoted as recording pairs; the recording pairs are each formed by a lead electrode (e.g. tip electrode 121, ring electrode 122, RV electrode 123, SVC electrode 124) and, preferably, a device electrode (e.g. can electrode 108). EGM samples from the recording pairs should be collected concurrently with a noisy sample from the sensing pair. All of the group of EGM samples may be collected simultaneously or in sequential sub-groups; if the EGM samples are collected in sequential sub-groups, each sub-group of samples from recording pairs should be concurrent with a noisy sample from the sensing pair. EGM sample collection may be triggered by a 'short' interval counter that counts up successive intervals of less than approximately 140 milliseconds between deflections of the sensing pair's EGM signal, which are detected like R-waves, for example, as seen between denoted R-waves in signal 32 of FIG. 3. A threshold for the count/number of intervals may be any predetermined number; according to an exemplary embodiment, EGM sample collection is triggered every twenty short intervals.

Figure 5A:
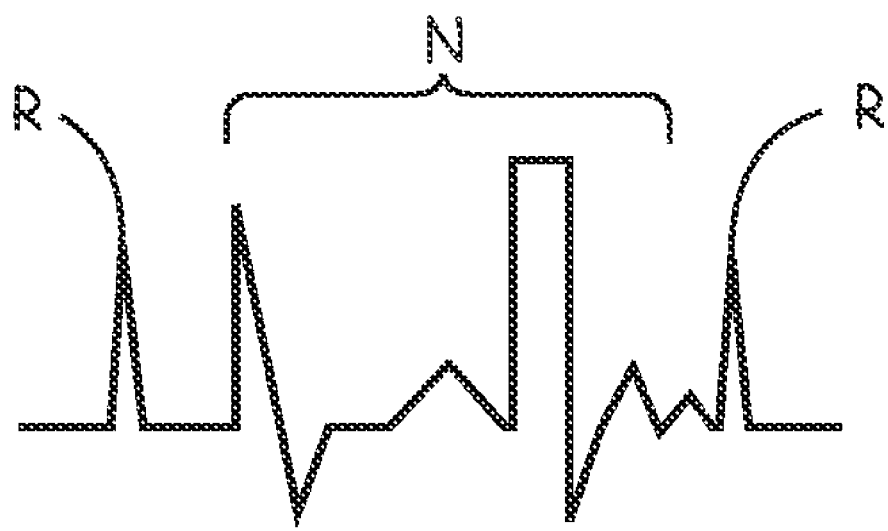
FIG. 5A is an exemplary noisy EGM sample.
Figure 5B:
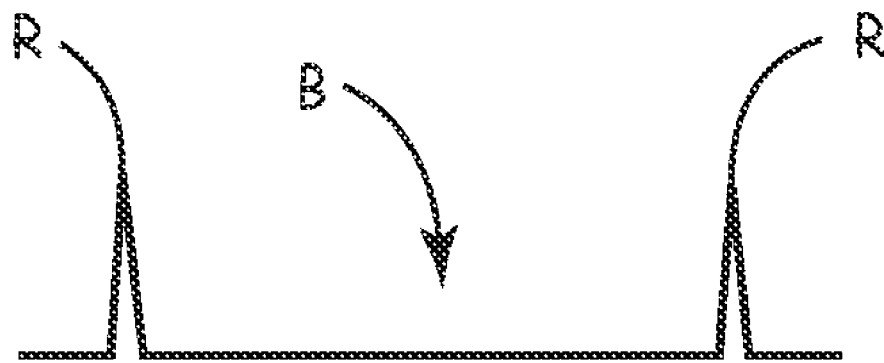
FIG. 5B is an exemplary 'clean' EGM sample.

After being collected, each of the EGM samples from the recording pairs are analyzed, per step 45, for the presence or absence of noise. According to some embodiments of the present invention, programmed instructions cause a device, for example IMD 10, to transfer the collected samples, per step 44, to an external device, for example, via telemetry, to device 11 (FIG. 1), for analysis, while, according to alternate embodiments, the analysis is performed within the implanted device. Suitable methods, known to those skilled in the art, for analyzing the sample EGM's include, without limitation, performing a frequency analysis algorithm to search for high frequency content, for example greater than approximately 512 Hz, that corresponds to non-physiologic noise (vs. physiologic, e.g. cardiac and/or muscular, noise), and performing a baseline detection algorithm at a point corresponding to a sensed noise event on the signal of the sensing pair, wherein a baseline is detected if an amplitude range of a number of points sampled from each sample is below a baseline threshold, for example 0.1 mV. If the former algorithm is used, noise is directly detected, whereas, if the latter is used, noise is indirectly detected when the baseline, indicating the absence of noise, is not detected. FIG. 5A is an exemplary sample EGM wherein a presence of noise N between R-waves R would be detected, either by frequency content or by inability to detect a baseline. FIG. 5B is an exemplary sample EGM wherein an absence of noise between R-waves R would be detected, either by frequency content or by the detection of a baseline B.

According to an alternate method of the present invention, step 41 of FIG. 4 may be incorporated into step 45, so that the group of EGM samples is collected, per step 43, whenever oversensing is detected, and the analysis of step 45 includes additional preliminary steps, per step 41, to determine if noise is the source of the oversensing, and to determine if the noise is system noise. If these preliminary steps confirm noise as system noise, then step 45 proceeds as described above.

Upon completion of step 45, each sample is categorized according to the presence or absence of noise, and the group of samples is analyzed, per step 47, to determine potential sources of noise. Table 1., shown below, summarizes various exemplary scenarios, #1-#10, for a group of recording pair EGM samples, wherein those on which noise is detected, for example, either directly or indirectly, as previously described, are marked with an 'X'; resulting conclusions regarding potential sources of noise are listed for each scenario. According to step 47, detection of a particular scenario from the exemplary scenarios #1-#10 leads to a determination of potential sources of system noise, which may be presented to the implantee and/or a clinician, either via a coded alarm emanating from IMD 10 or via a report prepared via external device 11 having received the information from IMD 10, for example, via telemetry.

for a RV defibrillation circuit including RV electrode 123 coupled to an RV conductor 53, SVC stands for a SVC defibrillation circuit including SVC electrode 124 coupled to an SVC conductor 54, and C stands for can 108 of IMD 10 acting as the device electrode which completes each recording pair. The device electrode C is preferably used in each recording pair because of a relatively low probability for the circuit including this electrode to be a source of noise, since the implanted device itself is not typically subjected to the relatively harsh mechanical stresses and strains to which the implanted lead is subjected. Thus, noise detected on a sample EGM from a recording pair that always includes the device electrode may, with relatively high confidence, be attributed to a component of the lead.

Figure 6:
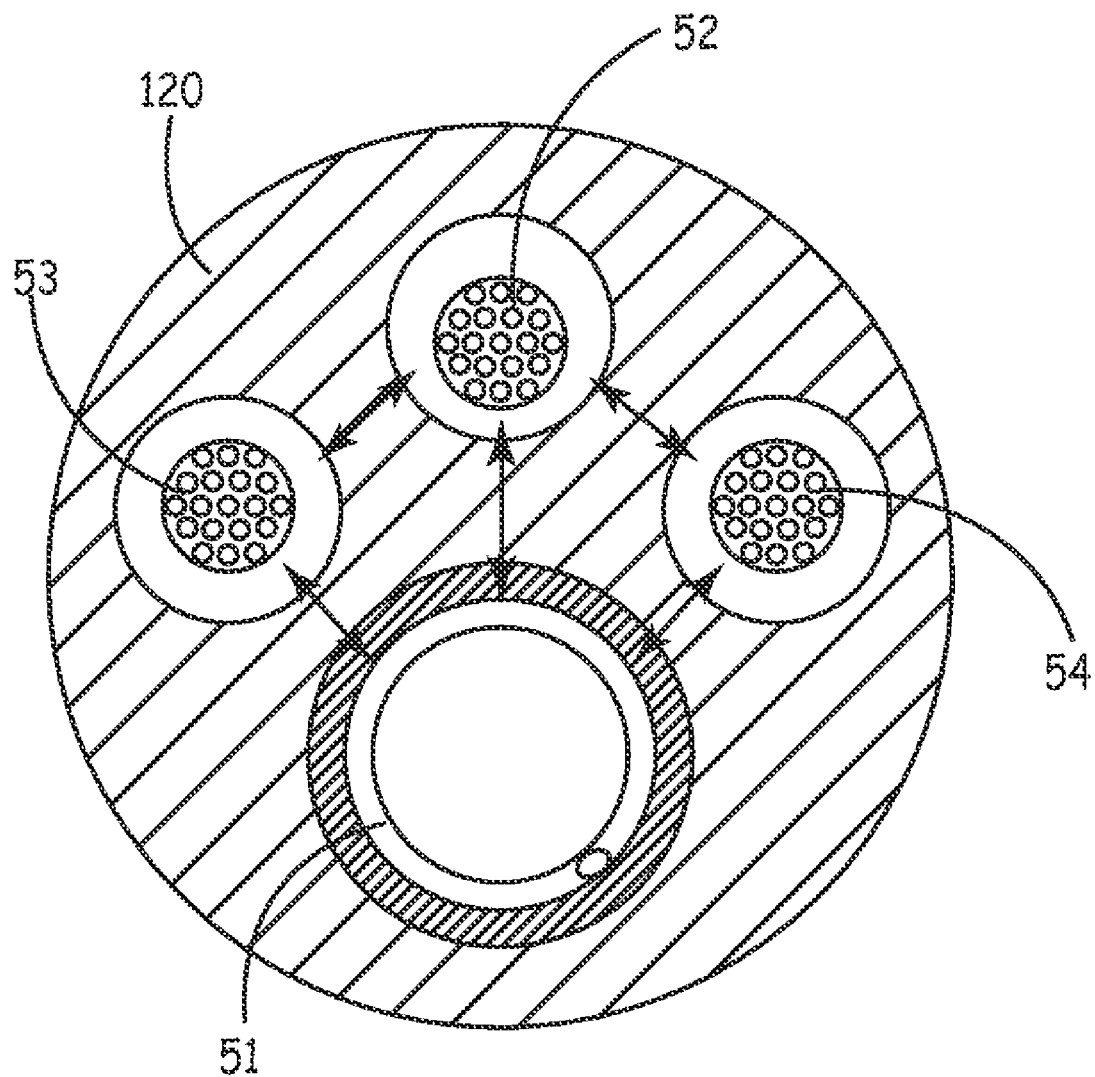
FIG. 6 is an exemplary cross-section of a portion of the system shown in FIG. 1.

Referring now to the far right hand column of Table 1., potential sources of noise for each scenario will be described in greater detail in conjunction with FIG. 6. According to scenario #1, the only recording pair having a sample EGM including noise is T-C so that step 47 determines that tip conductor 51 is a potential source of noise, for example, either due to a fracture in conductor 51 or an intermittent connection between conductor 51 and electrode 121 or an intermittent connection with device 10, either internal or external to lead 12, for example, in device header 109. Likewise, for ring conductor 52 in scenario #2. According to scenarios #3-#7, EGM samples from two recording pairs are found to include noise so that, in each of these scenarios, either multiple conductors independent of one another are determined to be the potential sources of the noise, or an insulation breach, which allows shorting between the conductors, for example, as illustrated within lead body 120 by the double-headed arrows in FIG. 6, is determined to be the potential source of noise. According to scenarios #8-#10, multiple insulation breaches, of one type or another, or multiple conductors independent of one another are determined to be the potential sources of

TABLE 1

| Scenario | Sensing Pair | T-C | R-C | RV-C | SVC-C | Potential Sources of Noise |
|---|---|---|---|---|---|---|
| #1 | X | X | | | | Tip conductor |
| #2 | X | | X | | | Ring conductor |
| #3 | X | X | X | | | Tip-Ring insulation or Tip and Ring conductors |
| #4 | X | X | | X | | Tip-RV insulation or Tip and RV conductors |
| #5 | X | X | | | X | Tip-SVC insulation or Tip and SVC conductors |
| #6 | X | | X | X | | Ring-RV insulation or Ring and RV conductors |
| #7 | X | | X | | X | Ring-SVC insulation or Ring and SVC conductors |
| #8 | X | X | X | X | | Tip-RV & Ring-RV or Ring-Tip insulation, or Tip, Ring and RV conductors |
| #9 | X | X | X | | X | Tip-SVC & Ring-SVC or Ring-Tip insulation, or Tip, Ring and SVC conductors |
| #10 | X | X | X | X | X | All insulation or all conductors |

Each recording pair, for example of lead 12 and device 10 (FIG. 1), are listed across a top of Table 1. With reference to FIG. 6, which is an exemplary cross-section of lead 12, in conjunction with FIG. 1 and Table 1., T stands for a tip electrode circuit including tip electrode 121 coupled to a tip conductor 51, R stands for a ring electrode circuit including ring electrode 122 coupled to a ring conductor 52, RV stands noise. According to some embodiments of the present invention, alternative potential noise sources, for example, as found in scenarios #3-#10, may be narrowed down by employing an impedance check of each circuit included in a recording pair having a noisy EGM sample. Those skilled in the art will appreciate that the results of impedance checks may point either to noise emanating from independent conductors, or to noise emanating from a pair of conductors intermittently contacting one another via an insulation breach.

If step 47 presents the potential noise source(s) of any of scenarios #1-#3, a clinician may decide to leave lead 12 implanted, for continued use of defibrillation coils 123 and 124, and to implant a pacing lead to take over for tip and ring electrodes 121, 122 of lead 12. However, if any of scenarios #4-#10 are presented, the clinician may opt to replace lead 12 with a new lead having a similar electrode configuration. Of course, for those scenarios where the potential source of noise can be narrowed down to one or more conductors, a check of the external connection between that conductor and device 10, for example, via the lead connector within header 109, should precede the implant of another lead, since, by comparison with lead implantation and/or extraction, correcting such a faulty connection, if found, is a relatively simple procedure.

It should be noted that the sensing pair of Table 1. is that pair from which a noisy signal was initially detected, and that there may be more than one sensing pair designated for monitoring, as previously described. With reference to Table 1., one can deduce that the sensing pair on whose signal system noise was detected is formed by tip electrode 121 and ring electrode 122, since, in every scenario, noise is also detected on the sample EGM from one or both of the T-C and R-C recording pairs. If, a signal from another sensing pair, for example, formed by RV electrode 123 and SVC electrode 124, were found with system noise, then scenarios #1-#3 shown in Table 1. would not be possible, and additional scenarios would include those in which both, and either, of the RV-C and SVC-C EGM samples include the noise.

In the foregoing detailed description, the invention has been described with reference to specific embodiments. However, it may be appreciated that various modifications and changes can be made without departing from the scope of the invention as set forth in the appended claims. For example, although methods of the present invention have been described in which electrode pairs include the electrodes of a single lead of the system, the scope of the invention is not so limited and alternate embodiments are contemplated in which electrode pairs include electrodes of a plurality of leads in the system.

The invention claimed is:

1. A medical system, comprising:
    an implantable device including a housing and a signal storage element enclosed in the housing, the housing forming an electrode of the device;
    an implantable medical electrical lead including a first electrode and a second electrode, the first and second electrodes forming a sensing pair when the lead is coupled to the device; and
    a device processor enclosed in the housing and programmed to detect noise on the sensing pair, identify the noise as system noise, and store at least one noisy EGM sample from the sensing pair and a concurrent EGM sample from each of a plurality of recording pairs in response to identifying the system noise, wherein the plurality of recording pairs includes a first pair formed by the first lead electrode and the device electrode, when the lead is coupled to the device, and a second pair formed by the second lead electrode and the device electrode, when the lead is coupled to the device.

2. The system of claim 1, further comprising an external device and wherein the device processor transfers each of the collected EGM samples to the external device for analysis.

3. The system of claim 1, wherein the device processor analyzes the EGM samples collected from the recording pairs to detect a presence or an absence of noise on each of the samples, and determines potential sources of noise based on the presence or absence of the noise on each of the samples.

4. The system of claim 1, wherein the first and second lead electrodes are a near-field pair forming the sensing pair.

5. The system of claim 1, wherein the first and second lead electrodes are a far-field pair forming the sensing pair.

6. The system of claim 1, wherein the lead further includes a third electrode and the plurality of recording pairs further includes a third pair formed by the third lead electrode and the device electrode.

7. The system of claim 6, wherein the lead further includes a fourth electrode and the plurality of recording pairs further includes a fourth pair formed by the fourth lead electrode and the device electrode.

8. A medical system, comprising:
    an implantable device including a housing, a processor enclosed in the housing, and a signal storage element enclosed in the housing, the housing forming an electrode of the device;
    an implantable lead including a plurality of electrodes forming a plurality of sensing pairs, when the lead is coupled to the device; and
    a device processor enclosed in the housing and programmed to detect noise on the one of the sensing pairs, identify the noise as system noise, and store at least one noisy EGM sample from a one of the plurality of sensing pairs and a concurrent EGM sample from each of a plurality of recording pairs in response to identifying the system noise, wherein the plurality of recording pairs are formed by each of the plurality of lead electrodes and the device electrode, when the lead is coupled to the device.

9. The system of claim 8, further comprising an external device and wherein the device processor transfers each of the collected EGM samples to the external device for analysis.

10. The system of claim 8, wherein the device processor analyzes the EGM samples collected from the recording pairs to detect a presence or an absence of noise on each of the samples, and determines potential sources of noise based on the presence or absence of the noise on each of the samples.

11. The system of claim 8, wherein:
    the plurality of lead electrodes includes a first electrode, a second electrode and a third electrode; and
    the plurality of sensing pairs includes a first pair formed by the first electrode and the second electrode and a second pair formed by the second electrode and the third electrode.

12. The system of claim 8, wherein:
    the plurality of lead electrodes includes a first electrode, a second electrode, a third electrode and a fourth electrode; and
    the plurality of sensing pairs includes a first pair formed by the first electrode and the second electrode, and a second pair formed by the third electrode and the fourth electrode.

13. A method to identify potential sources of noise emanating from an implanted portion of a medical system, the implanted portion including an implanted device and an implanted lead, the method comprising:
    detecting and identifying the noise as system noise on an EGM signal from a sensing pair formed by a first electrode of the lead and a second electrode of the lead;
    collecting at least one noisy EGM sample from the sensing pair and a concurrent EGM sample from each of a plurality of recording pairs in response to identifying the system noise, the plurality of recording pairs including a first pair formed by the first lead electrode and an electrode of the device and a second pair formed by the second lead electrode and the device electrode;

analyzing the EGM samples collected from the recording pairs to detect a presence or an absence of noise on each of the samples; and determining potential sources of the noise based on the presence or absence of the noise on each of the samples.

14. The method of claim 13, further comprising measuring an impedance of each circuit of each recording pair having an EGM sample on which the presence of noise was detected.

15. The method of claim 13, wherein the step of collecting occurs after the step of detecting and identifying the noise.

16. The method of claim 13, wherein the step of collecting comprises a first simultaneous collection of the EGM samples from a portion of the plurality of recording pairs and from the sensing pair, followed by a second simultaneous collection of the EGM samples from another portion of the plurality of recording pairs and from the sensing pair.

17. The method of claim 13, wherein the first and second lead electrodes are a near-field pair.

18. The method of claim 13, wherein the first and second lead electrodes are a far-field pair.

* * * * *